US00PP15202P2

(12) United States Plant Patent
Misato et al.

(10) Patent No.: US PP15,202 P2
(45) Date of Patent: Oct. 5, 2004

(54) ***MANDEVILLA* PLANT NAMED 'SUNMANDECOS'**

(50) Latin Name: *Mandevilla hybrida*
Varietal Denomination: Sunmandecos

(75) Inventors: Tomoya Misato, Omihachiman (JP); Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/409,704

(22) Filed: Apr. 9, 2003

(51) Int. Cl.[7] ..... A01H 5/00
(52) U.S. Cl. ..... Plt./232
(58) Field of Search ..... Plt./232

(56) References Cited

U.S. PATENT DOCUMENTS

| | | | |
|---|---|---|---|
| PP8,479 | P | 11/1993 | Henny |
| PP8,842 | P | 7/1994 | Henny |
| PP10,095 | P | 11/1997 | Henny |
| PP10,329 | P | 4/1998 | Wells |
| PP10,413 | P | 5/1998 | Alston |
| PP10,611 | P | 9/1998 | Alston |
| PP10,653 | P | 10/1998 | Gray |
| PP11,556 | P | 10/2000 | Tachibana et al. |
| PP11,624 | P | 11/2000 | Henny |
| PP11,787 | P2 | 2/2001 | Green et al. |
| PP12,123 | P2 | 10/2001 | Sperling |
| 6,300,547 | B1 | 10/2001 | Green et al. |
| PP12,238 | P2 | 11/2001 | Gray |
| PP12,813 | P2 | 7/2002 | Gray |

*Primary Examiner*—Kent Bell
(74) *Attorney, Agent, or Firm*—Burns, Doane, Swecker & Mathis, L.L.P.

(57) ABSTRACT

A new and distinct variety of *Mandevilla* plant is provided that was created through controlled cross-breeding. The female parent was a *Mandevilla amabilis×boliviensis* 'Sunmandeho' plant and the male parent was a *Mandevilla amabilis* 'Rose Giant' plant. The new variety exhibits a lianous growth habit and well tolerates heat. Attractive deep purplish-pink flowers having a vivid yellow throat are formed over an extended period of time. The flower petals curve outwards. Grayish-olive green leaves having an entire margin are formed. Plants of the new variety are well suited for growing in pots that are equipped with a support for climbing.

2 Drawing Sheets

Botanical/commercial classification: *Mandevilla hybrida*/*Mandevilla* Plant.
Varietal denomination: cv. 'Sunmandecos'.

BACKGROUND OF THE VARIETY

The present invention relates to a new and distinct variety of *Mandevilla* plant obtained from crossing *Mandevilla amabilis×boliviensis* 'Sunmandeho' plant (female) and *Mandevilla amabilis* 'Rose Giant' plant (male).

The *Mandevilla* is a popular plant and is used as a pot plant in the summer season or an indoor plant or a glasshouse plant. Only a limited number of varieties of *Mandevilla* plants are commercially available. Accordingly, this invention was aimed at obtaining a new variety having a large diameter flower, a purplish-pink flower, and a long flowering duration.

Initially, 100 seedlings were obtained in November 1998, from crossing a 'Sunmandeho' plant (U.S. Plant Pat. No. 11,556) as female parent and a 'Rose Giant' plant (non-patented in the United States) as pollen parent. These 100 seedlings were grown in a glasshouse from beginning in 1999 and one seedling was selected in view of its flower color and flowering duration. The selected seedling was propagated by the use of cuttings, and was then grown as a trial in a planter from May to November 2000. Finally the selected seedling was examined using the similar parent varieties 'Sunmandeho' and 'Rose Giant' for comparative purposes. As a result, it was concluded that this new *Mandevilla* is distinguishable from any other variety whose existence is known to us and is uniform and stable in its characteristics. This new variety has been named 'Sunmandecos'.

In the following description, the color-coding is in accordance with The R.H.S. Colour Chart of The Royal Horticultural Society, London, England.

The *Mandevilla amabilis×boliviensis* 'Sunmandeho' used as the female parent in the obtaining of this new variety 'Sunmandecos' is commercially available. The *Mandevilla amabilis×boliviensis* 'Sunmandeho' also is presently maintained at 863-1, Aza-Iketani, Ohmori-cho, Gamou-gun, Youkaichi, Shiga, Japan. The main botanical characteristics of *Mandevilla amabilis×boliviensis* 'Sunmandeho' are as follows:

Plant:
- *Growth habit.*—Lianous.

Stem:
- *Stem diameter.*—4.5 mm.
- *Stem color.*—Moderate Orange (R.H.S. Colour Chart No. 167D).
- *Lenticel.*—Not visible.
- *Branching.*—Few.
- *Internode length.*—13.0 cm.

Leaf:
- *Phyllotaxis.*—Opposite.
- *Whole shape of leaf.*—Elliptic.
- *Shape of leaf apex.*—Cuspidate.
- *Shape of leaf base.*—Acute.
- *Leaf length.*—11.0 cm.
- *Leaf width.*—5.0 cm.

*Leaf thickness.*—0.2 mm.
*Leaf margin.*—Entire.
*Color of mature leaf upper side.*—Medium olive green (R.H.S. Colour Chart No. 146A).
*Color of mature leaf reverse side.*—Medium yellow green (R.H.S. Colour Chart No. 146C).
*Variegation of mature leaf.*—Absent.
*Gloss of mature leaf upper side.*—Medium-strong.
*Pubescence of mature leaf upper side.*—Absent.
*Pubescence of mature leaf reverse side.*—Absent.
*Leaf petiole length.*—1.5 cm.
*Leaf petiole diameter.*—2.2 mm.
*Leaf petiole color.*—Brilliant yellow green (R.H.S. Colour Chart No. 145B).

Flower:
*Color of flower bud.*—Light yellow green (R.H.S. Colour Chart No. 149C).
*Length of peduncle.*—1.6 cm.
*Peduncle color.*—Strong yellow green (R.H.S. Colour Chart No. 144B).
*Flower shape.*—Single.
*Flower form.*—Perfectly open.
*Flower facing direction.*—Horizontal to slanted upward.
*Diameter of flower.*—11.0 cm.
*Flower height.*—9.0 cm.
*Floral tube length.*—5.5 cm.
*Color of flower upper side.*—Yellowish-white (R.H.S. Colour Chart No. 155C.)
*Color of inside surface of corolla throat.*—Vivid yellow (R.H.S. Colour Chart No. 15A).
*Color of flower outside.*—Yellowish-white (R.H.S. Colour Chart No. 158D).
*Whole shape of petal lobe.*—Orbicular.
*Shape of petal lobe apex.*—Cuspidate.
*Curvature of petal.*—Outwardly curved.
*Waving of petal.*—Medium.
*Petal length.*—5.5 cm.
*Petal width.*—6.0 cm.
*Petal number.*—5.

Reproductive organs:
*Pistil.*—Present.
*Pistil number.*—1.
*Stamen number.*—5.
*Anther color.*—Brilliant yellow (R.H.S. Colour Chart No. 153).
*Anther appendage.*—Absent.

Physiological and ecological characteristics:
*Flower number.*—Commonly 4–5 per cluster.
*Flower fragrance.*—Absent-weak.
*Fertility.*—Self fertile.
*Leaf abscission.*—The leaves fall when subjected to low temperature in late autumn.
*Flower abscission.*—The flowers commonly last approximately 7 to 10 days on the plant.
*Flowering duration.*—Long and substantially continuous (early June to early November in Japan).
*Cold tolerance.*—Low.
*Heat tolerance.*—High.
*Resistance to diseases.*—Medium.
*Resistance to pests.*—Medium.

The *Mandevilla amabilis* 'Rose Giant' used as the pollen parent in the obtaining of this new variety 'Sunmandecos' is commercially available. The *Mandevilla* plant *Mandevilla amabilis* 'Rose Giant' also is presently maintained at 863-1, Aza-Iketani, Ohmori-cho, Gamou-gun, Youkaichi, Shiga, Japan. The main botanical characteristics of *Mandevilla amabilis* 'Rose Giant' are as follows:

Plant:
*Growth habit.*—Lianous.

Stem:
*Stem diameter.*—6.0 mm.
*Stem color.*—Dark reddish-brown (R.H.S. Colour Chart No. 183A).
*Lenticel.*—Present.
*Branching.*—Few.
*Internode length.*—17.0 cm.

Leaf:
*Phyllotaxis.*—Opposite.
*Whole shape of leaf.*—Oblong.
*Shape of leaf apex.*—Mucronate.
*Shape of leaf base.*—Cordate.
*Leaf length.*—11.0 cm.
*Leaf width.*—7.0 cm.
*Leaf thickness.*—0.4 mm.
*Color of mature leaf upper side.*—Dark grayish-olive green (R.H.S. Colour Chart No. 139A).
*Color of mature leaf reverse side.*—Moderate yellow green (R.H.S. Colour Chart No. 147B).
*Variegation of mature leaf.*—Absent.
*Gloss of mature leaf upper side.*—Medium.
*Pubescence of mature leaf upper side.*—Present.
*Pubescence of mature leaf reverse side.*—Present.
*Leaf petiole length.*—1.0 cm.
*Leaf petiole diameter.*—3.5 mm.
*Leaf petiole color.*—Brilliant yellow green (R.H.S. Colour Chart No. 149B).

Flower:
*Color of flower bud.*—Strong purplish-pink (R.H.S. Colour Chart No. 62B).
*Length of peduncle.*—0.9 cm.
*Peduncle color.*—Vivid yellow green (R.H.S. Colour Chart No. 149A).
*Flower shape.*—Single.
*Flower form.*—Perfectly open.
*Flower facing direction.*—Horizontal to slanted upward.
*Diameter of flower.*—10.0 cm.
*Flower height.*—9.0 cm.
*Floral tube length.*—5.5 cm.
*Color of flower upper side.*—Deep purplish-pink (R.H.S. Colour Chart No. 155A).
*Color of inside surface of corolla throat.*—Yellowish-white (R.H.S. Colour Chart No. 155D).
*Color of flower outside.*—Deep purplish-pink (R.H.S. Colour Chart No. 55A).
*Whole shape of petal lobe.*—Orbicular.
*Shape of petal lobe apex.*—Cuspidate.
*Curvature of petal.*—Outwardly curved.
*Waving of petal.*—Weak.
*Petal length.*—5.5 cm.
*Petal width.*—6.0 cm.
*Petal number.*—5.

Reproductive organs:
*Pistil.*—Present.
*Pistil number.*—1.
*Stamen number.*—5.
*Anther color.*—Bright yellow (R.H.S. Colour Chart No. 15B).
*Anther appendage.*—Absent.

Physiological and ecological characteristics:

*Flower number.*—5–9 per cluster.
*Flower fragrance.*—Absent-weak.
*Fertility.*—Absent.
*Leaf abscission.*—The leaves fall when subjected to low temperature in late autumn.
*Flower abscission.*—The flowers commonly last approximately 7 to 10 days on the plant.
*Flowering time.*—Early.
*Flowering duration.*—Long (early June to late October in Japan).
*Cold tolerance.*—Low.
*Heat tolerance.*—High.
*Resistance to diseases.*—Medium.
*Resistance to pests.*—Medium.

This new variety of *Mandevilla* plant 'Sunmandecos' was asexually reproduced by the use of cuttings at Suntory Flowers Ltd., located at 863-1, Aza-Iketani, Ohmori-cho, Gamou-gun, Youkaichi, Shiga, Japan, and the homogeneity and stability thereof were thereby confirmed. The new variety reproduces true to type in successive generations of asexual reproduction.

SUMMARY OF THE NEW VARIETY

This new variety of *Mandevilla* plant possesses a lianous growth habit. The blooming period is from early June to early November in Japan and the flowering duration is long. When growing conditions are above 18° C., flowering is substantially continuous. The flower diameter is large. Both surfaces of the petals and the inside surface of corolla throat are deep purplish-pink. The leaves are grayish-olive green and are glabrous on both faces. The plant is highly tolerant to heat.

DETAILED DESCRIPTION OF THE NEW VARIETY

Figure 1:
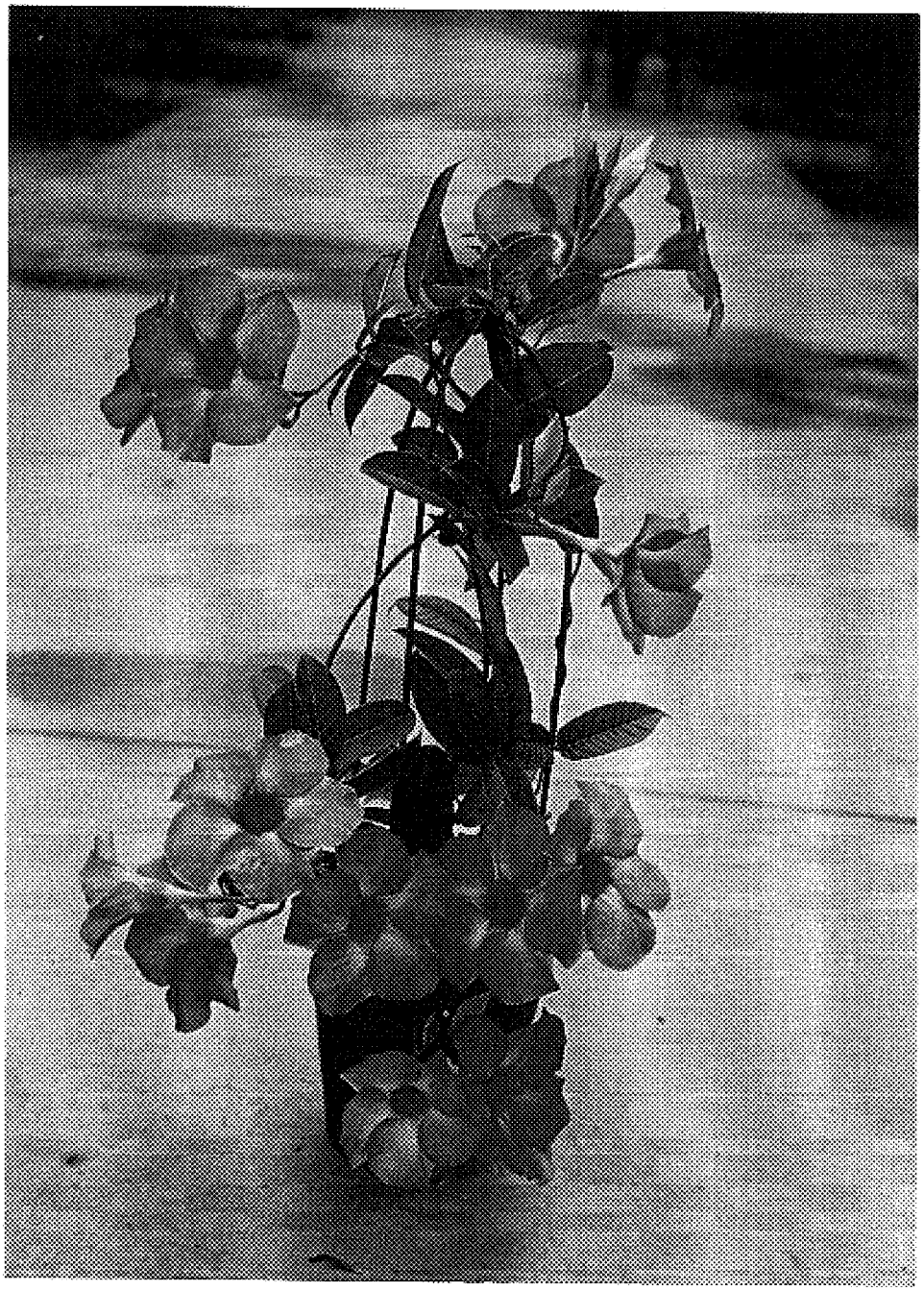
FIG. 1 is a photograph of the new 'Sunmandecos' variety of *Mandevilla* plant when growing in a pot.
Figure 2:
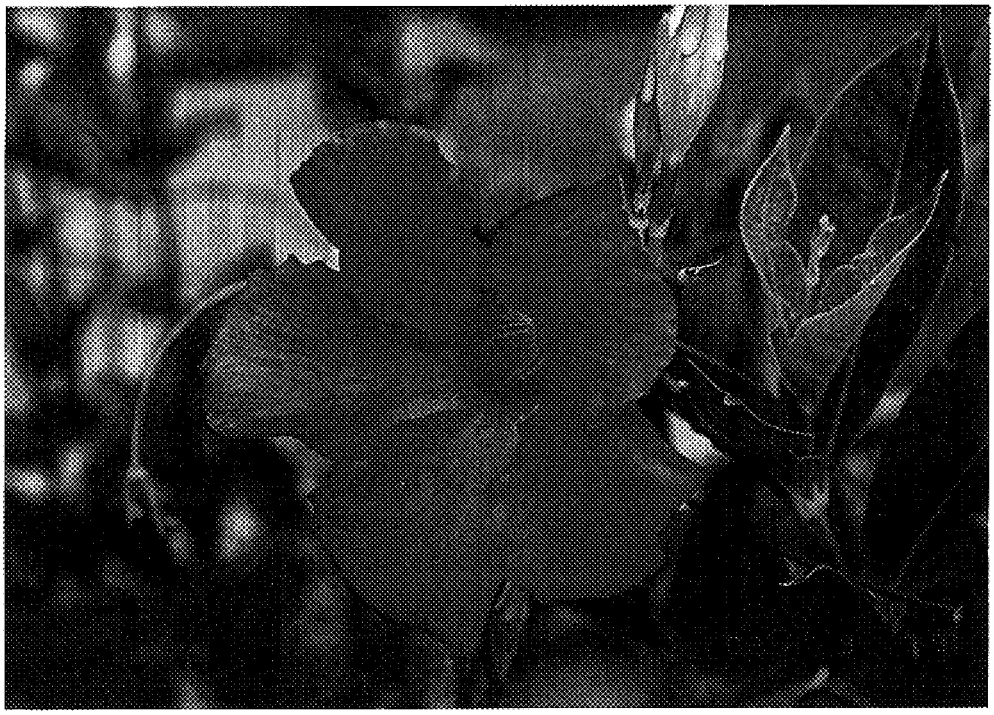
FIG. 2 is a close up photograph of a flower of the new 'Sunmandecos' variety of *Mandevilla* plant.

The botanical characteristics of the new 'Sunmandecos' variety of *Mandevilla* plant at an age of 10 months while growing in a 30 cm container in a glasshouse at Yakaichi-shi, Shiga, Japan are as follows:

Plant:

*Growth habit.*—Lianous.
*Height.*—Approximately 2.5 m (requires a support to keep upright).
*Width.*—Approximately 37 cm.

Stem:

*Stem diameter.*—Approximately 4.5 mm.
*Stem length.*—Approximately 2.5 m.
*Stem color.*—Grayish-olive green (R.H.S. Colour Chart No. 152B).
*Lenticel.*—Not visible.
*Branching.*—Few.
*Internode length.*—Approximately 10.5 cm.

Leaf:

*Phyllotaxis.*—Opposite.
*Whole shape of leaf.*—Oblong.
*Shape of leaf apex.*—Cuspidate.
*Shape of leaf base.*—Cordate.
*Leaf length.*—Approximately 11.0 cm.
*Leaf width.*—Approximately 4.5 cm.
*Leaf thickness.*—Approximately 0.5 mm.
*Leaf margin.*—Entire.
*Color of mature leaf upper side.*—Grayish-olive green (R.H.S. Colour Chart No. 137B).
*Color of mature leaf reverse side.*—Moderate yellow green (R.H.S. Colour Chart No. 146C).
*Variegation of mature leaf.*—Absent.
*Gloss of mature leaf upper side.*—Medium-strong.
*Pubescence of mature leaf upper side.*—Absent.
*Pubescence of mature leaf reverse side.*—Absent.
*Leaf petiole length.*—Approximately 1.0 cm.
*Leaf petiole diameter.*—Approximately 3.0 mm.
*Leaf petiole color.*—Strong yellow green (R.H.S. Colour Chart No. 143C).

Flower:

*Bud length.*—Approximately 8.0 cm.
*Bud diameter.*—Approximately 2.0 cm.
*Bud shape.*—Fusiform (spindle-shaped).
*Color of flower bud.*—Pale yellow green (R.H.S. Colour Chart No. 1D).
*Length of peduncle.*—Approximately 1.6 cm.
*Width of peduncle.*—Approximately 2.5 mm.
*Peduncle color.*—Strong brown (R.H.S. Color Chart No. 143C).
*Length of pedicel.*—Approximately 2 cm.
*Width of pedicel.*—Approximately 3 mm.
*Pedicel color.*—R.H.S. Colour Chart No. 147B.
*Flower number.*—Commonly approximately 9 in a cluster.
*Flower shape.*—Single, in a whorl of 5 petals.
*Flower form.*—Perfectly open.
*Flower facing direction.*—Horizontal to slanted upward.
*Diameter of flower.*—Approximately 10.5 cm.
*Flower height.*—Approximately 5.0 cm.
*Floral tube length.*—Approximately 4.5 cm.
*Floral tube diameter.*—Approximately 2 cm.
*Color of flower upper side.*—Deep purplish-pink (R.H.S. Colour Chart No. 61D).
*Color of upper surface of distal portion of corolla throat.*—Deep purplish-pink (R.H.S. Colour Chart No. 61D).
*Color of upper surface of basal portion of corolla throat.*—Vivid yellow (R.H.S. Colour Chart No. 15A).
*Color of flower lower surface.*—Pale yellow green (R.H.S. Colour Chart No. 1D).
*Overlapping of petals.*—By approximately 1 cm as illustrated in the photographs.
*Whole shape of petal lobe.*—Ovate.
*Shape of petal lobe apex.*—Rounded.
*Curvature of petal.*—Outwardly curved.
*Waving of petal.*—Medium.
*Petal margin.*—Entire.
*Petal length.*—Approximately 4.5 cm.
*Petal width.*—Approximately 4.9 cm.
*Flower fragrance.*—Absent-weak.
*Sepal number.*—5.
*Sepal length.*—Approximately 6 mm.
*Sepal width.*—Approximately 1 mm.
*Sepal shape.*—Narrowly ovate.
*Sepal apex.*—Pointed.
*Sepal base.*—Fused.

*Sepal margin.*—Entire.

*Sepal color.*—R.H.S. Colour Chart No. 147B on main body and R.H.S. Colour Chart No. 181A at apex.

Reproductive organs:

*Pistil.*—Present.

*Pistil number.*—1.

*Stamen number.*—5.

*Anther color.*—Light yellow (R.H.S. Colour Chart No. 15D).

*Anther appendage.*—Absent.

*Seed number.*—Approximately 200 per fruit.

*Seed length.*—Approximately 5 mm.

*Seed width.*—Approximately 1.5 mm.

*Seed color.*—R.H.S. Colour Chart No. 145A.

Physiological and ecological characteristics:

*Leaf abscission.*—The leaves fall when subjected to low temperature in late autumn.

*Flower abscission.*—The flowers commonly last approximately 7 to 10 days on the plant.

*Flowering time.*—Medium.

*Flowering duration.*—Long and substantially continuous (early June to early November in Japan).

*Cold tolerance.*—The plant has survived temperatures as low as 4° C. The lowest temperature for plant survival has not been evaluated.

*Heat tolerance.*—High, with the plant growing well at temperatures up to at least 30° C. The upper temperature for plant survival has not been evaluated.

*U.S.D.A. hardiness zone*—No. 11.

*Resistance to diseases.*—No particular susceptibility to plant diseases has been encountered during observations to date.

*Resistance to pests.*—Slight damage by mites sometimes has been observed. No serious damage by white flies and aphids has been encountered during observations to date.

This new variety of *Mandevilla* plant, 'Sunmandecos' is most suitable for potting in the summer season or for use as an outdoor plant or as a glasshouse plant. This new variety exhibits a lianous growth habit and can be readily trained to grow on a wire or other upright support.

We claim:

1. A new and distinct variety of *Mandevilla* plant that exhibits:

(a) a lianous growth habit, (b) forms attractive large deep purplish pink flowers over an extended period of time having petals that curve outwards, (c) displays grayish olive green leaves, and (d) well tolerates heat;

substantially as shown and described.

* * * * *